United States Patent [19]

Leal et al.

[11] Patent Number: 4,459,709
[45] Date of Patent: Jul. 17, 1984

[54] ARTIFICIAL LIMB PROSTHESIS

[75] Inventors: Joseph M. Leal; James M. Malone, both of Tucson, Ariz.

[73] Assignee: U.S. Manufacturing Company, Pasadena, Calif.

[21] Appl. No.: 321,447

[22] Filed: Nov. 16, 1981

[51] Int. Cl.³ .............................................. A61F 1/08
[52] U.S. Cl. .................................................. 3/2; 3/17 R
[58] Field of Search ..................... 3/2, 4, 17 R, 17 SS, 3/18, 19, 20, 21; 128/82, 83, 85, 87 R, 89 R, 91 R, 90; 264/DIG. 30, 257, 258, 222

[56] References Cited

U.S. PATENT DOCUMENTS

| | | | |
|---|---|---|---|
| 2,103,511 | 12/1937 | Brown | 3/17 R |
| 3,389,700 | 6/1968 | Whyte | 128/91 R |
| 3,998,219 | 12/1976 | Mercer et al. | 128/89 R |
| 4,128,903 | 12/1978 | Marsh et al. | 3/21 |

FOREIGN PATENT DOCUMENTS 267988 3/1927 United Kingdom ................ 3/17 SS
487641 1/1976 U.S.S.R. .................................. 3/19

Primary Examiner—Richard J. Apley
Assistant Examiner—David J. Isabella
Attorney, Agent, or Firm—Christie, Parker & Hale

[57] ABSTRACT

An artificial limb which is designed primarily for temporary use, such as for sports, while taking a shower, where the artificial limb is subjected to dirt, sand, or water. The artificial limb is constructed of a plastic tubular member which is split or bifurcated at one end to form a group of projecting fingers which define a cup-shaped region. A socket is formed of wrapped casting tape with the fingers being embedded in the socket walls during the wrapping operation.

5 Claims, 7 Drawing Figures

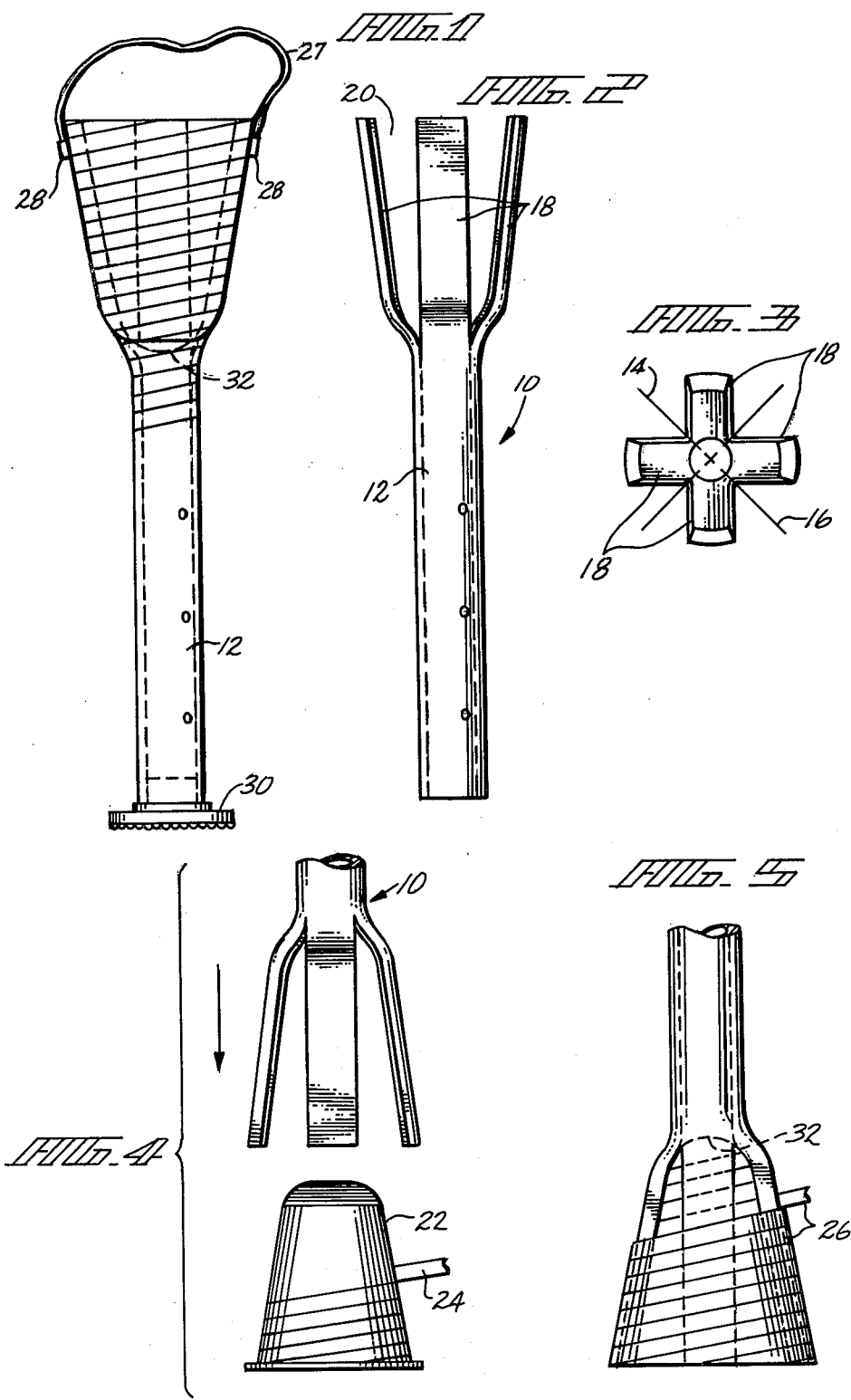

ARTIFICIAL LIMB PROSTHESIS

FIELD OF THE INVENTION

This invention relates to artificial limbs, and more particularly, to a prosthesis useful as an artifical leg or arm.

BACKGROUND OF THE INVENTION

Artificial legs used by amputees take a wide variety of forms from the old wooden peg leg to the more modern mechanically sophisticated devices which provide the user with almost full control of his movements. However, such modern prosthetic devices often have complex mechanical parts which must be kept clean and may be damaged by dirt, grit, moisture or corrosive chemicals. There is, therefore, a need of a simple, comfortable prosthetic device which can be used as an artifical leg in special situations, such as when taking a shower, going to the beach, participating in certain sports activities, or similar situations where the prosthetic device is exposed to dirt, sand, and potentially corrosive materials, such as salt, soap, or the like.

SUMMARY OF THE INVENTION

The present invention is directed to a prosthetic device which functions as an artificial limb that is light in weight and is easily installed, but has no moving parts and can be used in all types of adverse environmental conditions which would be damaging to the more expensive prosthetic devices. The present invention is directed to an improved method of manufacturing such a prosthetic device which allows it to be comfortably fitted to the user and results in an inexpensive, lightweight, and rugged artificial limb that can be used in water or other potentially damaging conditions. This is accomplished, in brief, by providing a plastic tubular member with one end divided into a plurality of individual fingers which are spread to form an enlarged cup-shaped region. The user's stump or a mold made of the stump is wrapped with casting tape and then inserted into the cup-shaped region of the tubular member. Additional casting tape is then wrapped around the outside of the fingers to form a shell having a stump-shaped socket for receiving the user's stump.

BRIEF DESCRIPTION OF THE DRAWINGS

For a better understanding of the present invention, reference should be made to the accompanying drawings, wherein:

FIG. 1 is a front view of an artificial limb of the present invention;
FIG. 2 is a side view of the main structural member;
FIG. 3 is a top view of the main structural member;
FIGS. 4–5 show the sequence of steps used in manufacturing the prosthetic device;
FIG. 6 is a side view, partly broken away, showing the cup-shaped inner wall of the socket and the separate outer layer of casting tape; and
FIG. 7 is a top view of the device shown in FIG. 6.

DETAILED DESCRIPTION

Referring to the drawings in detail, the numeral 10 indicates generally the main structural member which is made from a length of plastic tubing, such as, for example, a standard 1 ½" or 2" PVC pipe. One end of the tube 12 is cut lengthwise along two mutually perpendicular planes, indicated at 14 and 16 in FIG. 3. Thus the end of the tube is divided into four arcuate sections which are formed into radially offset fingers 18. The fingers define a substantially cup-shaped region 20. The fingers may be formed by heating the plastic material where it is to be bent, so that the material can be bent and will assume and hold its desired shape.

After the offset fingers are formed, the main structural member 10 is incorporated into an artificial leg in the manner best illustrated in FIGS. 4 and 5. Preferably a mold is first made which simulates the leg or arm stump of the amputee being fitted with the device. This can be done, for example, by first making a negative mold of the stump and then filling the negative mold with plaster of paris or other suitable material to form a positive mold. A positive mold is indicated at 22. While the use of a mold is preferred, the artificial limb can be constructed directly using a person's stump as the mold. The term "mold" as used herein refers to either a cast mold or the stump used as a mold.

The mold or stump is covered by a protective sock, which is pulled over the mold. The mold or stump is then wrapped with a single layer 24 of a commercially available casting tape. Casting tape consists of a fabric strip impregnated with a resin which, when soaked in water and exposed to air, dries or sets up to to form a rigid plastic wall. Casting tape is sold, for example, under the trade name "SCOTCHCAST" by the Orthopedic Products Division of 3M Company, St. Paul, MN. The sock allows the casting tape to be withdrawn from the mold or stump after it hardens. The hardened casting tape forms a rigid cup-shaped shell.

After the initial layer 24 of casting tape is wrapped on the mold, the fingers 18 of the structural member 10 are lowered around the mold, with the mold extending into the cup-shaped region 20. Once the fingers are in position, at least two additional layers 26 of casting tape are wound over the fingers and the previously wound layer of casting tape 24 and down along the tubular portion of the member 10. Typically, two outer wrapped layers are all that are required to complete the construction of the artificial limb. After the outer layers of casting tape are allowed to harden, the finished assembly is removed from the mold or stump 22. The other end of the pipe 12 is then cut off to the proper length and a rubber foot 30 is secured to the lower end of the tube 12. When used as an arm, the rubber foot is replaced by a suitable "hand", such as hook, blade, or the like.

FIG. 6 shows the finished device and illustrates, in particular, the cup-shaped inner wall of the rigid shell formed by the hardened inner layer 24 of casting tape. This view also shows the outer layer 26 of casting tape which bonds to the inner layer in the arcuate spaces between the fingers 18 to form a solid wall of the finished socket. This view also shows that the inner layer is separate from the outer layer at the bottom of the socket.

FIG. 7 is a top view of the finished socket. This view shows how the outer layer of casting tape bonds to the inner layer in the spaces between the fingers 18. The fingers are embedded in the inner and outer layers of the hardened casting tape. This view also illustrates the minute perforations 34 inherent in the woven casting tape layer which provide porosity to air and water at the cup-shaped bottom portion of the shell formed by the inner layer of hardened casting tape.

The finished device is used as an artificial leg or arm by inserting the stump of the user in the socket formed by the hardened casting tape after the mold is removed. The artificial limb can be held in place by a harness arrangement 27 which goes around the upper part of the stump or around the body of the user and includes straps which attach to the upper end of the artificial limb. Plastic clips 28 may be cemented, riveted or otherwise secured to the wrappings during the manufacturing process and provide a means of attaching the straps to the artificial limb.

It will be seen that the artificial limb of the present invention provides a prosthetic aid useful as an artificial leg or arm. It can be easily attached to the stump of an amputee whether the amputation is above or below the joint. The artificial limb provides a temporary orthotic aid useful as as an artificial limb. It has no moving parts, it is inexpensive to make, and it is not adversely affected by dirt, sand, or water. The single layer of casting tape at the bottom 32 of the socket forms a slightly porous wall after it hardens, allowing some air and water to migrate through the wall so that water will not accumulate in the bottom of the socket, and the device remains comfortable to wear even when it is exposed to moisture and perspiration. Because the artificial limb is inexpensive and easy to make, it can be readily replaced if it is damaged from severe use or becomes excessively soiled or uncomfortable to wear.

What is claimed is:

1. A method for making an artificial limb for attachment to a stump of an amputee, comprising the steps of:
    wrapping a layer of casting tape around a mold of the stump;
    allowing the casting tape to harden and form a cup-shaped shell with a rigid wall formed by the hardened casting tape itself, in which the inner surface of the wall conforms to the shape of the mold and at least a bottom portion of the wall is porous to air and water;
    inserting the hardened shell of casting tape into an enlarged cup-shaped region formed by a plurality of circumferentially spaced-apart fingers at the end of a main structural member; and
    wrapping an outer layer of casting tape around the outside of the fingers and the shell and allowing the outer layer of casting tape to harden so that the outer layer of casting tape is integral with the hardened casting tape shell in the spaces between the fingers to form a solid wall of a socket at the end of the main structural member, in which the fingers are embedded between the shell and outer layer of casting tape, and each of the fingers is positioned to overlap the stump when the latter is inserted into the socket portion of the artificial limb.

2. The method according to claim 1, in which the main structural member is a tubular member.

3. The method according to claim 2, in which the main structural member is made of plastic.

4. The method according to claim 1, including attaching a strap to the casting tape forming the socket for securing the artificial limb to the wearer.

5. The method according to claim 1, including cutting the other end of the main structural member to the desired length and inserting a foot member of elastomeric material in said other end of the main structural member.

* * * * *

UNITED STATES PATENT AND TRADEMARK OFFICE
CERTIFICATE OF CORRECTION

PATENT NO. : 4,459,709

DATED : July 17, 1984

INVENTOR(S) : Joseph M. Leal; James M. Malone

It is certified that error appears in the above-identified patent and that said Letters Patent is hereby corrected as shown below:

Column 1, line 17, change "of" to --for--. In the drawings, after Fig. 5, insert Figs. 6 and 7 as illustrated below:

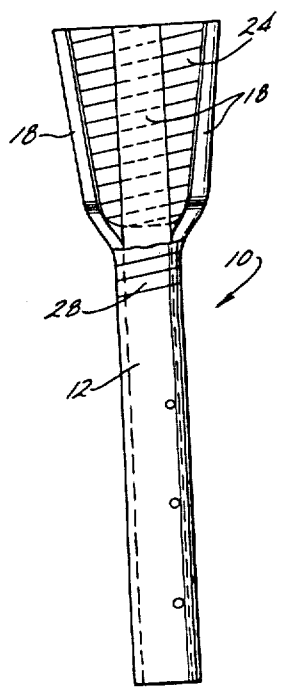

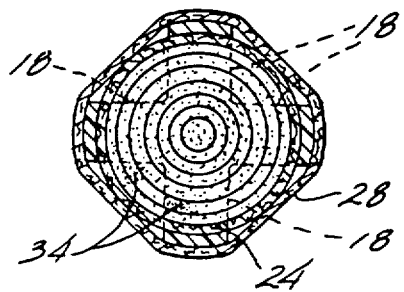

Signed and Sealed this

Twenty-second Day of October 1985

[SEAL]

Attest:

DONALD J. QUIGG

Attesting Officer

Commissioner of Patents and
Trademarks—Designate